United States Patent [19]

Jacquet et al.

[11] Patent Number: 4,906,617

[45] Date of Patent: Mar. 6, 1990

[54] PHARMACEUTICAL COMPOSITIONS CONTAINING SATURATED AROMATIC PEROXIDES

[75] Inventors: Bernard Jacquet, Antony; Michel Hocquaux, Paris; Didier Semeria, Gif sur Yvette; Didier Saint-Leger, Paris, all of France

[73] Assignee: L'Oreal, Paris, France

[21] Appl. No.: 102,493

[22] Filed: Sep. 29, 1987

[30] Foreign Application Priority Data

Sep. 30, 1986 [FR] France .................. 86 13605

[51] Int. Cl.⁴ .................. A61K 31/75; A61K 31/70
[52] U.S. Cl. .................. 514/24; 514/29; 514/699; 514/714; 514/859
[58] Field of Search .................. 514/714, 859, 24, 29

[56] References Cited

U.S. PATENT DOCUMENTS

4,364,940 12/1982 Neiss et al. .................. 424/230

FOREIGN PATENT DOCUMENTS

| 133554 | 2/1985 | European Pat. Off. |
| 2018589 | 10/1979 | United Kingdom |
| 2088717 | 6/1982 | United Kingdom |
| 2110088 | 6/1983 | United Kingdom |
| 2150436 | 7/1985 | United Kingdom |

*Primary Examiner*—Leonard Schenkman
*Attorney, Agent, or Firm*—Cushman, Darby & Cushman

[57] ABSTRACT

A pharmaceutical or cosmetic composition contains as an active principle a peroxide having an aromatic radical and a saturated group and having the formula

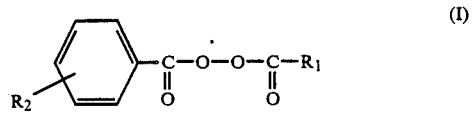

(I)

wherein $R_1$ represents linear or branched alkyl having 3 to 17 carbon atoms, substituted or not by one or more halogens, interrupted or not by a carbonyl group and carrying a terminal carboxylic acid group esterified or not or $R_1$ represents cycloalkyl having 5 to 10 carbon atoms, and $R_2$ represents hydrogen, halogen, —$CF_3$, methoxy, ethoxy or acyl having 2 to 16 carbon atoms.

The composition is usefully employed in the treatment of various dermatoses including acne.

13 Claims, No Drawings

PHARMACEUTICAL COMPOSITIONS CONTAINING SATURATED AROMATIC PEROXIDES

BACKGROUND OF THE INVENTION

The present invention relates to new pharmaceutical or cosmetic compositions for the treatment of various dermatoses, and principally for the treatment of acne, containing, as the active principle, a peroxide having an aromatic radical and a saturated group.

Acne, as is well known, is a cutaneous disorder, polymorph (several types of lesions existing in a given person) occurring generally at puberty and disappearing spontaneously in the majority of cases at about age 20 to 25.

Acne is found, more particularly, in areas rich in sebaceous glands, which evidences a certain dependence of this dermatosis vis-a-vis sebum, a synthesis product of the gland.

The increase in hormonal activity occurring at puberty, causes a hyperactivity of the sebaceous glands and the sebum thus generated flows then towards the cutaneous surface by the pilosebaceous duct.

The ethiopathogenesis of acne, although poorly defined, finds its origin in the formation of a characteristic lesion, the comedo, which results in the obstruction of the pilosebaceous duct as a result of diskeratinization of the zone of the infundibilium of the duct.

This obstruction has for a major effect a modification of the viscosity of the sebum and the physico-chemical characteristics of the environment (pH, oxygen vapor pressure . . . ).

This modification permits hyperproliferation of resident cutaneous strains, principally *propionibacterium acnes*, anaerobic or aero-tolerant strains.

This bacterial hyperproliferation has for a consequence the liberation in the environment of certain proteases of bacterial origin which cause a lysis of the follicular sac and thus the liberation of inflammatory compounds in the dermis which in turn effects an inflammatory type reaction of the organism.

The essential elements of the pathology of acne are then:
an increase in sebaceous excretion,
a disorder in the keratinization of the pilosebaceous duct and
a bacterial hyperproliferation, principally of *propionibacterium acnes*.

A good anti-acne agent capable of treating acne in an effective manner must then exhibit the following activities:

(a) a keratolytic and comedolytic activity so as to avoid hyperkeratosis of the follicles and to permit removal of comedos, (b) a bacteriostatic activity so as to inhibit the activity of *propionibacterium acnes* and (c) a sebostatic activity so as to inhibit hyperseborrhea.

Numerous anti-acne agents have been proposed but none can claim to possess all of the activities which are required for the effective treatment of acne and without exhibiting, moreover, secondary or side effects.

Among these known agents, the most well known unquestionably is benzoyl peroxide which is an antibacterial agent also possessing keratolytic properties.

Nonetheless, the use of benzoyl peroxide is not without certain disadvantages due to its instability, its reactivity and its side effects.

Benzoyl peroxide exhibits, as a side effect, a certain aggressiveness capable of causing frequent intolerances during treatment such as itching, and this even when it is employed at relatively weak concentrations.

The present invention provides a new anti-acne composition for the treatment of various states of acne whose keratolytic, comedolytic and bacteriostatic activity is greater than that of compositions based on benzoyl peroxide.

The compounds employed in the composition according to the present invention, because of their lipophilic character, are more penetrating and generative during passage through the skin than benzoic acid or its derivatives. These compositions on the one hand exhibit a well-known keratolytic character and on the other hand lower the pH to a level which is favorable to the inhibition of the action of *propionibacterium acnes*.

The present invention has for an object a pharmaceutical or cosmetic composition containing as the active principle at least one peroxide having an aromatic radical and a saturated group and having the formula

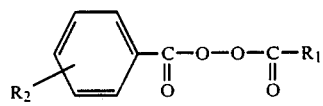

(I)

wherein $R_1$ represents linear or branched alkyl having 3 to 17 carbon atoms, substituted or not by one or more halogens, interrupted or not by a carbonyl group and being able to have a terminal carboxylic acid group esterified or not, or $R_1$ represents cycloalkyl having from 5 to 10 carbon atoms, and $R_2$ represents hydrogen, halogen, $-CF_3$, methoxy, ethoxy or acyl having 2 to 16 carbon atoms.

Pharmacologic studies carried out using the active compounds employed in the compositions of the present invention have evidenced a keratolytic and comedolytic activity clearly greater than that of benzoyl peroxide.

In Formula I, above, the aromatic radical is preferably phenyl, p-chlorophenyl, m-chlorophenyl, p-methoxy phenyl or o-, m- or p-trifluoromethyl phenyl.

The linear or branched alkyl having 3 to 17 carbon atoms is, preferably, propyl, pentyl, isopentyl, heptyl, nonyl, undecyl or heptadecyl.

The cycloalkyl radical having 5 to 10 carbon atoms is, preferably, cyclopentyl, cyclohexyl, adamantyl, norbornyl, 4-(1,1-dimethyl ethyl) cyclohexyl, decahydronaphthyl or 7,7-dimethyl bicyclo [2-2-1]hept-1-yl.

Representative peroxides of Formula I include the following:

(1) hexanoyl benzoyl peroxide,
(2) octanoyl benzoyl peroxide,
(3) decanoyl benzoyl peroxide,
(4) lauroyl benzoyl peroxide,
(5) palmitoyl benzoyl peroxide,
(6) octanoyl m-chlorobenzoyl peroxide,
(7) 2-methyl-1-oxopropyl benzoyl peroxide,
(8) 3-methyl-1-oxobutyl benzoyl peroxide,
(9) 3,3-dimethyl-1-oxobutyl-3-chlorobenzoyl peroxide,
(10) 1-oxoheptyl-3-chlorobenzoyl peroxide,
(11) 2-methyl-1-oxobutyl-3-chlorobenzoyl peroxide,

(12) 2-chloro-2-methyl-1-oxopropyl benzoyl peroxide,
(13) 5-bromo-1-oxopentyl benzoyl peroxide,
(14) 2-bromo-1-oxohexyl benzoyl peroxide,
(15) 2-chloro-2-ethyl-1-oxohexyl benzoyl peroxide,
(16) 2-chloro-1-oxobutyl-3-chlorobenzoyl peroxide,
(17) 2-chloro-3-methyl-1-oxobutyl-3-chlorobenzoyl peroxide,
(18) 2-chloro-3,5,5-trimethyl-1-oxohexyl-3-chlorobenzoyl peroxide,
(19) 3-carboxypropionyl benzoyl peroxide,
(20) 4-carboxybutyryl benzoyl peroxide,
(21) 2-ethoxycarbonyl-2-methyl butyryl benzoyl peroxide,
(22) cyclohexylcarbonyl benzoyl peroxide,
(23) (7,7-dimethyl bicyclo [2-2-1]hept-1-yl) carbonyl benzoyl peroxide,
(24) cyclohexyl carbonyl 3-chlorobenzoyl peroxide,
(25) [4-(1,1-dimethyl ethyl) cyclohexyl]carbonyl 3-chlorobenzoyl peroxide,
(26) (bicyclo [2-2-1]hept-2-yl) carbonyl 3-chlorobenzoyl peroxide and
(27) 4-oxopentanoyl benzoyl peroxide.

The peroxides of Formula I, of which certain ones are known, are obtained in accordance with conventional methods described in the literature and in particular the following documents and articles.

"Organic peroxides", Ed. D. Swern, 1970, 1971 and 1972;

K. Rübsamen, Chem. Ber. 102, 1290, (1969);

D. Denney, J. Org. Chem. Vol. 30, 3760, (1965);

THE CHEMISTRY OF PEROXIDES, ED. Saul Patai, (1983), John Wiley Sons; and

M Feldhues - H.J. Schafer, Tetrahedon, 41, (19) 4195–4212 and 4213–4235, (1985).

In accordance with these methods, an acid chloride is reacted either with perbenzoic acid or a derivative of perbenzoic acid, in the presence of a base, or with a sodium salt thereof, or even with an aromatic acid chloride, optionally substituted, in the presence of $H_2O_2$ and a base.

Various examples of the preparation of the peroxides employed in the compositions according to the invention are given hereafter as an illustration of the invention.

The compositions according to the present invention can be provided in various forms and principally in the form of an ointment, gel, emulsion, lotion or a stick.

The term "ointment" covers formulations such as creams containing absorbable lipophilic bases, for example, petrolatum, lanolin, polyethylene glycols and mixtures thereof.

The emulsion, be they oil-in-water or water-in-oil emulsions, are prepared by dispersing the peroxides, in accordance with the present invention, in the aqueous phase before emulsification.

The weight ratio of the fatty phase to the aqueous phase is generally between 95:5 and 25:75.

Representative oils capable of constituting the oil or fatty phase include such products as:

(1) animal oils such as lanolin and perhydrosqualene,
(2) vegetable oils such as sweet almond oil, avocado oil, ricin oil, olive oil, grapeseed oil, poppy oil, colza oil, peanut oil, corn oil, turnsole oil, hazelnut oil, jojoba oil, safflower oil, wheat germ oil, karite butter and the fat of Shorea robusta; and
(3) mineral oils such as paraffin oil, and silicone oils soluble in other oils.

There can also be employed fatty alcohols such as cetyl alcohol or certain synthetic products such as, for example, saturated esters and principally isopropyl palmitate, isopropyl myristate, butyl myristate, cetyl myristate, hexadecyl stearate, glycerol stearate, polyethylene glycol stearate and ethyl palmitate as well as triglycerides of octanoic and decanoic acids, cetyl ricinoleate, purcellin oil and hydrogenated polyisobutylene.

The oily phase of the emulsions can also contain certain waxes and principally carnauba wax, beeswax, ozokerite or candellila wax.

These compositions, in the form of emulsions, can also contain other components such as preservatives, sequesterants, pigments, perfumes, dyes, sunscreen agents, emulsion stabilizers such as magnesium sulfate, filler such as talc, nylon powders, starch or polyethylene.

However, the carrier or vehicle and components which can react in an undesirable fashion with the peroxides employed in the compositions of the present invention must be avoided.

The gels are semi-solid preparations obtained by gelification of a suspension of the peroxides using a gelling agent such as "Bentone gel", sold by N.L. Industries, for an oily phase or for an aqueous phase, cross-linked polyacrylic acid such as that sold by Goodrich under the trade names "CARBOPOL 940" and CARBOPOL 941"and employed in neutralized form or even cellulose derivatives.

If desired, there can be introduced into the gel a nonionic surfactant such as, for example, a polyoxyethylenated alcohol having from 4 to 20 ethylene oxide units or sorbitan esters, which provides a better dispersion and availability of the peroxide.

There can also be incorporated a solvent such as a lower alphatic alcohol, for example, ethanol, in an amount ranging from 0.5 to 30 weight percent, based on the total weight of the composition or a preservative, a perfume or a dye.

The compositions according to the present invention can also include a humectant agent in an amount ranging from 1 to 20 weight percent, based on the total weight of the composition. Representative humectants include glycerine, sorbitol and propylene glycol.

In the compositions, such as described above, the peroxide in accordance with the present invention, is generally present in an amount ranging from 0.1 to 20 weight percent, and preferably from 1 to 10 weight percent, based on the total weight of the composition.

In accordance with a preferred embodiment, the peroxide can be combined with at least one topically applicable anti-acne substance, and preferably an antibiotic substance.

In accordance with this embodiment, the antibiotic substance is generally present in an amount ranging from 0.5 to 5 weight percent based on the total weight of the composition.

Representative preferred antibiotics include erythromycin, clindamycin and lincomycin, their esters and their salts.

In accordance with another embodiment, the peroxide can be combined with at least one other keratolytic agent such as, for example, salicylic acid, an anti-fungus agent or antiinflammatory agent.

In the treatment of acne, the compositions such as defined above are applied at least once a day to the lesions at a rate of 0.5 to 10mg/cm$^2$, the duration of the treatment lasting from about 2 to 14 weeks depending on the severity of the cutaneous disorder.

The following non-limiting examples are given to illustrate the present invention.

A. Examples of the Preparation of Peroxides

EXAMPLE 1

Preparation of hexanoyl benzoyl peroxide

Compound of Formula I wherein $R_1 = -(CH_2)_4-CH_3$ and $R_2 = H$

To 3.2 grams of sodium perbenzoate (0.02 mole) covered with 50 ml of anhydrous methylene chloride, there are added at $-30°$ C., under an inert gas, 2.96 grams of hexanoic acid chloride (1.1.eq) over a 10 minute period. The reaction mixture is stirred at $-15°$ C. for 2 hours and then washed with a bicarbonate solution until neutral.

After drying the organic phase on sodium sulfate and evaporation of the methylene chloride, in the cold and under a vacuum, 4.8 g of a crude oil are obtained which is then chromatographed on a silica column (eluant: 5/1 mixture of hexane/methylene chloride).

After evaporation of the elution solvent under a vacuum and in the cold, 4.05 g of a pure oil are recovered (86% yield).

The $NMR_1H$ spectrum conforms to the expected structure. IR Spectrum: Bands at $1810^{cm-1}$ and $1780^{cm-1}$ (diacylated peroxide).

Peroxide index: 97 %.

EXAMPLE 2 - Preparation of octanoyl benzoyl peroxide

Compound of Formula I wherein $R_1 = -(CH_2)_6-CH_3$ and $R_2 = H$

In accordance with the same procedures as those described in Example 1 and by using 3.6 g of octanoic acid chloride, 4.4 grams of a pure oil are obtained (83% yield). The $NMR_1H$ spectrum conforms to the expected structure. IR Spectrum: Bands at $1810^{cm-1}$ and $1780^{cm-1}$ (diacylated peroxides).

Peroxide index: 97%.

EXAMPLE 3

Preparation of decanoyl benzoyl peroxide

Compound of Formula I wherein $R_1 = -(CH_2)_6-CH_3$ and $R_2 = H$

In accordance with the same procedures as those described in Example 1 and by using 4.2 g of decanoic acid chloride, 4.9 g of a pure oil are obtained (84% yield). The $NMR_1H$ spectrum conforms to the expected structure. IR Spectrum: Bands at $1810^{cm-1}$ and $1780^{cm-1}$ (diacylated peroxides)

Peroxide index: 98%.

EXAMPLE 4

Preparation of octanoyl-m-chlorobenzoyl peroxide

Compound of Formula I wherein $R_1 = -(CH_2)_8-CH_3$ and $R_2 = m-Cl$

To 3 g of an 85% solution of m-chloroperbenzoic acid in 70 ml of anhydrous ether, there are added at $-30°$ C., under an inert gas, 2.6 g (1.1 eq.) of octanoic acid chloride. After the slow addition of 1.4 ml of pyridine, stirring is continued at $-30°$ C. for about 1 hour.

After washing with water until neutral and drying the organic phase on sodium sulfate, the ether is evaporated under a vacuum and in the cold. 5.1 g of a crude oil are obtained and then the oil is chromatographed on a silica column (eluant: 95/5 mixture of hexane/ethyl acetate). After evaporation of the elution solvent under a vacuum and in the cold, 4.2 g of pure oil are recovered (95% yield).

The $NMR_1H$ spectrum conforms to the expected structure. IR spectrum: Bands at $1810^{cm-1}$ and $1780^{cm-1}$ (diacylated peroxides)

Peroxide index: 98.3%.

Examples of Composition

EXAMPLE 1

An anti-acne stick having the following composition is prepared:

| Carnauba wax | 6.00 g |
| --- | --- |
| Ozokerite | 6.00 g |
| Cetyl alcohol | 2.00 g |
| Anhydrous lanolin | 9.50 g |
| Hydrogenated polyisobutylene | 60.00 g |
| Titanium oxide | 2.00 g |
| Red iron oxide | 2.00 g |
| Yellow iron oxide | 1.50 g |
| Brown iron oxide | 1.00 g |
| Octanoyl m-chlorobenzoyl peroxide | 10.00 g |

EXAMPLE 2

An anti-acne gel having the following composition is prepared:

| "Carbopol 934" by Goodrich | 0.60 g |
| --- | --- |
| Triethanolamine, sufficient amount for pH = 6.5 | 0.40 g |
| Mixture of polyethylene glycol stearate and glycol stearate, sold by Gatefosse under the trade name "TEFOSE 63" | 3.00 g |
| Purcellin oil | 5.00 g |
| Lauroyl benzoyl peroxide | 5.00 g |
| Sodium salt of EDTA | 0.05 g |
| Purified water, sufficient amount for | 100.00 g |

EXAMPLE 3

An anti-acne cream having the following composition is prepared:

| Stearate of polyethylene glycol 50, sold by Atlas under the trade name "MYRJ 53" | 4.00 g |
| --- | --- |
| Glycerol monostearate | 0.70 g |
| Cetyl alcohol | 2.50 g |
| Self-emulsifiable wax, sold by Henkel under the trade name "SINNOWAX SX" | 4.00 g |
| Petrolatum oil | 10.00 g |
| "Carbopol 940" by Goodrich | 0.20 g |
| Triethanolamine, sufficient amount for pH = 6.5 | 0.20 g |
| Octanoyl benzoyl peroxide | 1.00 g |
| Sodium salt of ethylene diamine tetracetic acid | 0.05 g |
| Water, sufficient amount for | 100.00 g |

What is claimed is:

1. An anti-acne composition having improved keratolytic activity for application to the skin comprising, in a pharmaceutically or cosmetically acceptable and topically applicable carrier, as an active principle, at least one peroxide having an aromatic radical and a saturated group and having the formula

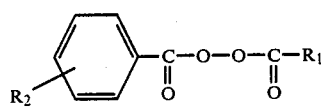

(I)

wherein $R_1$ represents linear or branched alkyl having 3 to 17 carbon atoms substituted or not by one or more halogens, interrupted or not by carbonyl and having a terminal carboxylic acid group esterified or not, or $R_1$ represents cycloalkyl having 5 to 10 carbon atoms, and $R_2$ represents hydrogen, halogen, $-CF_3$, methoxy, ethoxy, or acyl having 2 to 16 carbon atoms, said peroxide being present in an amount ranging from 0.1 to 20 weight percent based on the total weight of said composition.

2. The composition of claim 1 wherein said aromatic radical is phenyl, p-chlorophenyl, m-chlorophenyl, p-methoxyphenyl or o-, m- or p-trifluoromethylphenyl.

3. The composition of claim 1 wherein said linear or branched alkyl having 3 to 17 carbon atoms is propyl, pentyl, isopentyl, heptyl, nonyl, undecyl or heptadecyl.

4. The composition of claim 1 wherein said cycloalkyl having 5 to 10 carbon atoms is cyclopentyl, cyclohexyl, adamantyl, norbornyl, 4-(1,1-dimethyl ethyl) cyclohexyl, decahydronaphthyl or 7,7-dimethyl bicyclo [2-2-1]hept-1-yl.

5. The composition of claim 1 wherein $R_1$ represents linear or branched alkyl having 5 to 11 carbon atoms and $R_2$ represents hydrogen or chlorine.

6. The composition of claim 1 wherein said peroxide is selected from the group consisting of
(1) hexanoyl benzoyl peroxide,
(2) octanoyl benzoyl peroxide,
(3) decanoyl benzoyl peroxide,
(4) lauroyl benzoyl peroxide,
(5) palmitoyl benzoyl peroxide,
(6) octanoyl m-chlorobenzoyl peroxide,
(7) 2-methyl-1-oxopropyl benzoyl peroxide,
(8) 3-methyl-1-oxobutyl benzoyl peroxide,
(9) 3,3-dimethyl-1-oxobutyl-3-chlorobenzoyl peroxide,
(10) 1-oxoheptyl-3-chlorobenzoyl peroxide,
(11) 2-methyl-1-oxobutyl-3-chlorobenzoyl peroxide,
(12) 2-chloro-2-methyl-1-oxopropyl benzoyl peroxide,
(13) 5-bromo-1-oxopentyl benzoyl peroxide,
(14) 2-bromo-1-oxohexyl benzoyl peroxide,
(15) 2-chloro-2-ethyl-1-oxohexyl benzoyl peroxide,
(16) 2-chloro-1-oxobutyl-3-chlorobenzoyl peroxide,
(17) 2-chloro-3-methyl-1-oxobutyl-3-chlorobenzoyl peroxide,
(18) 2-chloro-3,5,5-trimethyl-1-oxohexyl-3-chlorobenzoyl peroxide,
(19) 3-carboxypropionyl benzoyl peroxide,
(20) 4-carboxybutyryl benzoyl peroxide,
(21) 2-ethoxycarbonyl-2-methyl butyryl benzoyl peroxide,
(22) cyclohexylcarbonyl benzoyl peroxide,
(23) (7,7-dimethyl bicyclo [2-2-1]hept-1-yl) carbonyl benzoyl peroxide,
(24) cyclohexyl carbonyl 3-chlorobenzoyl peroxide,
(25) [4-(1,1-dimethyl ethyl) cyclohexyl]carbonyl 3chlorobenzoyl peroxide,
(26) (bicyclo [2-2-1]hept-2-yl) carbonyl 3-chlorobenzoyl peroxide and
(27) 4-oxopentanoyl benzoyl peroxide.

7. The composition of claim 1 wherein said peroxide is present in an amount ranging from 1 to 10 weight percent based on the total weight of said composition.

8. The composition of claim 1 in the form of an ointment, emulsion, gel, lotion or stick.

9. The composition of claim 1 which also includes at least one antibiotic.

10. The composition of claim 9 wherein said antibiotic is erythromycin, clindamycin, lincomycin, their esters or their salts.

11. The composition of claim 1 which also includes at least one other keratolytic agent, anti-fungus agent or antiinflammatory agent.

12. The composition of claim 1 which also includes one or more of a preservative, pigment, humectant, perfume, dye, surfactant, thickening agent, filler, solvent, stabilizer, sunscreen agent or sequesterant.

13. A method for treating acne comprising topically applying to the skin of a person suffering from acne an amount, effective for the treatment of acne, of the composition of claim 1.

* * * * *